United States Patent [19]

Milkowski et al.

[11] 4,216,167
[45] Aug. 5, 1980

[54] 1,3 DIAMINOPROPANE DERIVATIVES

[75] Inventors: Wolfgang Milkowski, Burgdorf; Renke Budden, Peine; Siegfried Funke, Hanover; Rolf Hüschens, Hanover; Hans-Günther Liepmann, Hanover; Werner Stühmer, Eldsagsen; Horst Zeugner, Hanover, all of Fed. Rep. of Germany

[73] Assignee: Kali-Chemie Aktiengesellschaft, Hanover, Fed. Rep. of Germany

[21] Appl. No.: 729,142

[22] Filed: Oct. 4, 1976

Related U.S. Application Data

[63] Continuation-in-part of Ser. No. 558,969, Jun. 20, 1975, abandoned, which is a continuation-in-part of Ser. No. 355,987, May 3, 1973, abandoned, and a continuation-in-part of Ser. No. 355,986, May 1, 1973, Pat. No. 3,998,809.

[30] Foreign Application Priority Data

May 3, 1972 [DE] Fed. Rep. of Germany ....... 2221558

[51] Int. Cl.$^2$ ............... C07C 103/74; C07C 103/75
[52] U.S. Cl. ............... 260/558 D; 260/340.3; 260/558 S; 260/558 P; 260/559 R; 260/559 T; 560/106; 560/231
[58] Field of Search ......... 260/558 P, 558 D, 559 R, 260/558 S

[56] References Cited

U.S. PATENT DOCUMENTS

| | | | |
|---|---|---|---|
| 2,721,214 | 10/1955 | Troutman | 260/558 P X |
| 2,721,215 | 10/1955 | Goldberg et al. | 260/558 P |
| 2,785,200 | 3/1957 | Moore | 260/558 D |
| 3,576,868 | 4/1971 | Kaegi | 260/558 P |
| 3,957,870 | 5/1976 | Main | 260/559 R X |
| 3,975,443 | 8/1976 | Harper et al. | 260/558 D |
| 4,021,224 | 5/1977 | Pallos et al. | 260/558 D X |
| 4,059,621 | 11/1977 | Vincent et al. | 260/558 R |

FOREIGN PATENT DOCUMENTS

| | | | |
|---|---|---|---|
| 2166116 | 2/1973 | Fed. Rep. of Germany | 260/558 P |
| 42-17009 | 9/1967 | Japan | 260/558 P |

*Primary Examiner*—John Doll
*Attorney, Agent, or Firm*—Michael J. Striker

[57] ABSTRACT

A 1,3 diaminopropane derivative having the formula I

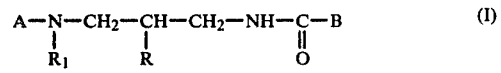

in which

R$_1$ is hydrogen, methoxyethyl, benzyl or alkyl of at most 6 carbon atoms or is cycloalkyl of 3 to 6 carbon atoms, R is hydroxy, acetoxy or benzoxy, and A and B are phenyl or phenyl substituted with one to three identical or different members selected from the group consisting of halogen, alkyl, alkoxy, the alkyl or alkoxy moieties of the latter two groups having at most 4 carbon atoms, or phenyl substituted by nitro, trifluoromethyl, methylthio, or ethylenedioxy, or an acid addition salt of said diaminopropane derivative.

19 Claims, No Drawings

1,3 DIAMINOPROPANE DERIVATIVES

CROSS-REFERENCE TO RELATED APPLICATIONS

This application is a continuation-in-part of application Ser. No. 355,986, filed by the same inventors and entitled "Benzodiazepine Derivatives and Process of Making Them", filing date May 1, 1973, now U.S. Pat. No. 3,998,809. This application is furthermore a continuation-in-part of application Ser. No. 588,969, filed by the same inventors in respect of "Benzodiazocine Derivatives and Process of Making the Same" on June 20, 1975, now abandoned, which latter application is a continuation-in-part of application Ser. No. 355,987, filed May 3, 1973, now abandoned.

BACKGROUND OF THE INVENTION

In the just-noted application Ser. No. 355,986 2,3-dihydro-1H-1,4-benzodiazepins have been disclosed of the general formula

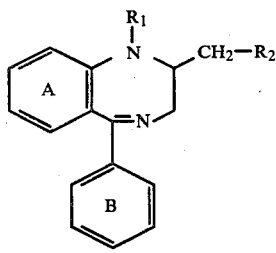

(II)

In these compounds $R_1$ may have various meanings but usually is methyl. $R_2$ may likewise have various meanings but in most cases is hydroxy, alkoxy, halogen, etc. The phenyl radical indicated by B is usually substituted in the 2-position by chloro but may also have other substituents. The phenyl radical indicated as A may be substituted in the 7, 8 or 9-position by halogen, nitro or trifluoromethyl, methylthio, alkyl or alkoxy.

These compounds are valuable tranquilizers with excellent anticonvulsive, muscle relaxant and sedative activity and a desirable ratio between these different activities. They also have a low toxicity.

As disclosed in the two applications, Ser. Nos. 355,986 and 588,969, these 1,4-benzodiazepins can be made by starting from the present 1,3 diaminopropane derivatives which themselves are novel and are claimed herein.

SUMMARY OF THE INVENTION

The process of the invention accordingly relates to 1,3 diaminopropane derivative having the formula I

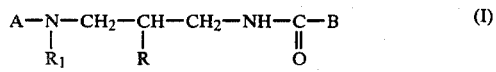

(I)

in which
  $R_1$ is hydrogen, methoxyethyl, benzyl or alkyl of at most 6 carbon atoms or is cycloalkyl of 3 to 6 carbon atoms,
  R is hydroxy, acetoxy or benzoxy,
  A and B are phenyl or phenyl substituted with one to three identical or different members selected from the group consisting of halogen, alkyl, alkoxy, the alkyl or alkoxy moieties of the latter two groups having at most 4 carbon atoms, or phenyl substituted by nitro, trifluoromethyl, methylthio, or ethylenedioxy,
or an acid addition salt of said diaminopropane derivative. Accordingly the compounds of the invention more specifically are $N_1$-aryl-$N_2$-aroyl-2-hydroxy-1,3-diamino-propanes. Instead of 2-hydroxy they may also be 2-acetoxy or 2-benzoxy compounds.

DISCUSSION OF THE INVENTION AND PREFERRED EMBODIMENTS

Preferably, in the formula I shown above
  $R_1$ is hydrogen, methyl, ethyl, methoxyethyl, benzyl, or cyclopropylmethyl,
  R is hydroxy, acetoxy or benzoxy,
  A is phenyl, 4-chlorophenyl, 4-fluorophenyl, 4-methylphenyl, 4-methoxyphenyl, 4-methylthiophenyl, 3,4-dimethoxyphenyl or 3,4 ethylenedioxyphenyl,
  B is phenyl, 2-methylphenyl, 2-chlorophenyl, 2-bromophenyl, 2-fluorophenyl, 2-nitrophenyl, 2-(trifluoromethyl)phenyl, 3-(trifluoromethyl)phenyl, 2,3-dichloro-phenyl, 2,4-dichlorophenyl, 2,6-dichlorophenyl, 3,4-dichlorophenyl, 3,4-dimethoxyphenyl or 3,4,5-trimethoxyphenyl.

The diaminopropane derivatives of the present invention may be made for instance as follows:

A diaminopropane having the following formula

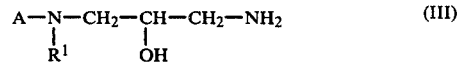

(III)

in which $R^1$ and A have the same significance as in formula I above, is reacted with a carboxylic acid or a derivative thereof that is capable of reacting with the diamine to form an acyldiamine. Such carboxylic acids and carboxylic acid derivatives, such as carboxylic acid esters, carboxylic acid anhydrides, mixed carboxylic acid anhydrides, or carboxylic acid halides, have the following formulae

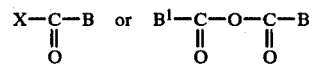

in which formulae B has the same significance as in formula I above, $B^1$ is the same as B or is lower alkyl or lower alkoxy, and X is hydroxyl, halogen or lower alkoxy.

The reaction of the diamine with the carboxylic acid or derivative thereof can be carried out in an inert solvent in the presence of an acid acceptor or acid-binding agent, preferred examples of which are tertiary amines such as triethylamine and pyridine. If the acid-binding agent is used in excess it can serve at the same time as the inert solvent in the reaction. The reaction can however also be carried out in an inert solvent in the absence of an acid-binding agent.

Suitable inert solvents for use for this purpose are for instance methylene chloride (dichloromethane), chloroform, acetone, dioxane, benzene, toluene and chlorobenzene.

The temperature at which the reaction is conducted depends on the particular carboxylic acid or derivative thereof and is between $-30°$ C. and the boiling point of the solvent. The reaction can be carried out at an atmospheric or a superatmospheric pressure.

If equimolecular quantities of the diamine having the formula III and the carboxylic acid or derivative thereof are reacted, the principal product is an acyldiamine having the formula I hereinbefore in which R is a hydroxyl radical. The hydroxyl radical can then be esterified with acetic anhydride or benzoyl chloride or other suitable carboxylic acid anhydrides, esters, or halides to produce the desired ester in which R is an acetoxy, benzoxy, or similar radical. When 2 mols of benzoyl chloride, for example, are used for each mol of diamine, the product is an acyldiamine having the formula I hereinbefore in which R is the benzoxy radical.

After completion of the reaction it is possible to further treat the reaction product in conventional form and for instance to isolate the product as a base or to react it with an inorganic or organic acid to form a salt thereof. The crude base can for instance be obtained from the reaction product by extraction with suitable solvents, for instance chloroform, and concentration by evaporation of the extract. The purification of the crude base can be carried out by customary means such as use of active charcoal or aluminum oxide.

Acids suitable for making the addition salts of the diaminopropane of formula I are preferably hydrochloric, hydrobromic, sulfuric, or orthophosphoric acid.

The acid addition salts serve the same purposes as the free bases but have the advantage of being water soluble.

The following are examples illustrating the making of the diaminopropane of the present invention:

EXAMPLE 1

To a solution of 128 grams of N-methyl-N-(2-hydroxy-3-aminopropyl)-4'-chloroaniline and 200 milliliters of chloroform containing 84 milliliters of triethylamine was slowly added with stirring 69.5 milliliters of benzoyl chloride. After 24 hours the chloroform solution was washed with water and dried over anhydrous sodium sulfate. The chloroform was then distilled off at a subatmospheric pressure and the crude product that was thus obtained was recrystallized from benzene. There were thus obtained 142.5 grams of N-methyl-N-(2-hydroxy-3-benzoylaminopropyl)-4'-chloroaniline having a melting point of 136°-137° C.

EXAMPLE 2

Into a solution of 59 grams of N-methyl-N-(2-hydroxy-3-aminopropyl)-4'-chloroaniline in 1 liter of chloroform containing 85 milliliters of triethylamine there were slowly stirred 70 milliliters of benzoyl chloride. The mixture was then heated under gentle reflux for a period of 4 hours and further treated as described hereinbefore in Example 1. The crude product was recrystallized from isopropanol and there were thus obtained 61 grams of N-methyl-N-(2-benzoxy-3-benzoylaminopropyl)-4'-chloroaniline having a melting point of 145°-148° C.

EXAMPLE 3

Into a solution of 45.4 grams of N-methyl-N-[2-hydroxy-3-(3',4',5'-trimethoxybenzoyl)aminopropyl]aniline in 250 milliliters of pyridine there were slowly stirred 250 milliliters of acetic anhydride. After 48 hours the solution was poured into water and extracted with chloroform. The chloroform extract was concentrated by evaporation at a subatmospheric pressure and the residue was recrystallized from diethyl ether. There was thus obtained N-methyl-N-[2-acetoxy-3-(3',4',5'-trimethoxybenzoyl)aminopropyl]aniline having a melting point of 90°-92° C.

EXAMPLE 4

A solution of 10 g 3,4-dimethoxybenzoic acid in 100 ml methylenechloride is successively reacted upon cooling by ice with 9 ml triethylamine and 9 g chloroformic ethylester. After 30 min. 10 g N-methyl-N-(2-hydroxy-3-aminopropyl)-4'-chloroaniline are added in batches. After 24 hours the solution is stirred into ice water, and the methylenechloride phase is separated, dried on $Na_2SO_4$ and concentrated by evaporation in a vacuum. The residue is taken up in 100 ml methanol and is heated for 6 hours to 60° C. with 20 ml 20% sodium hydroxide. The methanol is thereafter distilled off in a vacuum, the aqueous phase is extracted with chloroform, the chloroform phase is washed with water and is then concentrated by evaporation in a vacuum. The residue is recrystallized from ether/ethanol. There is thus obtained 4 g N-methyl-N-[2-hydroxy-3-(3',4'-dimethoxybenzoyl)-aminopropyl]-4'-chloroaniline having a melting point of 118°-121° C.

EXAMPLE 5

A solution of 10 g N-methyl-N-(2-hydroxy-3-aminopropyl)-4'-chloroaniline in 200 ml methylenechloride is successively reacted, upon cooling by ice, with 11 ml triethylamine and a solution of 12.2 g 2'-fluorobenzoic acid anhydride in 100 ml methylenechloride. After 24 hours the solution is stirred into ice water as in Example 4 and is in the same manner further processed and recrystallized from benzene. There are obtained 5.4 g of N-methyl-N-[2-hydroxy-3-(2'-fluorobenzoyl)-aminopropyl]-4'-chloroaniline having a melting point of 105°-107° C.

In exactly the same manner as described in Examples 1 to 5 the following compounds were made.
N-methyl-N-[2-hydroxy-3-(3',4'-dimethoxybenzoyl)-aminopropyl]-3',4'-dimethoxyaniline, (oil);
N-methyl-N-[2-hydroxy-3-(3',4'-dimethoxybenzoyl)-aminopropyl]-3',4'-ethylenedioxyaniline, (oil);
N-methyl-N-[2-hydroxy-3-(2'-chlorobenzoyl)-aminopropyl]-3',4'-ethylenedioxyaniline, m.p. 105°-107° C.;
N-methyl-N-(2-hydroxy-3-benzoylaminopropyl)-4'-methylthioaniline, m.p. 141°-142° C.;
N-methyl-N-[2-hydroxy-3-(2',6'-dichlorobenzoyl)-aminopropyl]-4'-chloroaniline, (oil);
N-methyl-N-[2-hydroxy-3-(2',3'-dichlorobenzoyl)-aminopropyl]-4'-chloroaniline, m.p. 91°-95° C.;
N-methyl-N-[2-hydroxy-3-(2'-methylbenzoyl)-aminopropyl]-4'-chloroaniline, m.p. 108°-113° C.;
N-methyl-N-[2-hydroxy-3-(2'-bromobenzoyl)-aminopropyl]-4'-chloroaniline, m.p. 118°-123° C.;
N-methyl-N-[2-hydroxy-3-(2'-nitrobenzoyl)-aminopropyl]-4'-chloroaniline, m.p. 132°-133° C.;
N-ethyl-N-(2-hydroxy-3-benzoylaminopropyl)-4'-chloroaniline, m.p. 121°-123° C.;
N-β-methoxyethyl-N-(2-hydroxy-3-benzoylaminopropyl)-4'-chloroaniline, m.p. 120°-122° C.;
N-methyl-N-[2-hydroxy-3-(3',4',5'-trimethoxybenzoyl)-aminopropyl]-aniline, m.p. 126°-129° C.;
N-methyl-N-(2-hydroxy-3-benzoylaminopropyl)-4'-fluoroaniline, m.p. 115°-118° C.;
N-methyl-N-[2-hydroxy-3-(2'-fluorobenzoyl)-aminopropyl]-4'-chloroaniline, m.p. 105°-107° C.;
N-methyl-N-(2-hydroxy-3-benzoylaminopropyl)-aniline, m.p. 100°-103° C.;

N-(2-hydroxy-3-benzoylaminopropyl)-4'-chloroaniline, m.p. 175°–177° C.;

N-cyclopropylmethyl-N-(2-hydroxy-3-benzoylaminopropyl)-4'-chloroaniline, m.p. 110°–112° C.;

N-methyl-N-(2-acetoxy-3-benzoylaminopropyl)-aniline, (oil);

N-methyl-N-[2-acetoxy-3-(2'-fluorobenzoyl)-aminopropyl]-4'-chloroaniline, (oil);

N-methyl-N-[2-hydroxy-3-(2'-chlorobenzoyl)-aminopropyl]-4'-chloroaniline, m.p. 113°–115° C.;

N-methyl-N-[2-hydroxy-3-(2'-trifluoromethylbenzoyl)-aminopropyl]-4'-chloroaniline, m.p. 107°–109° C.;

N-methyl-N-[2-hydroxy-3-(3',4'-dimethoxybenzoyl)-aminopropyl]-4'-chloroaniline, m.p. 118°–121° C.;

N-methyl-N-[2-hydroxy-3-(3',4'-dichlorobenzoyl)-aminopropyl]-4'-chloroaniline, m.p. 115°–117° C.;

N-methyl-N-(2-benzoyloxy-3-benzoylaminopropyl)-aniline, m.p. 129°–130° C.;

N-methyl-N-[2-hydroxy-3-(2',4'-dichlorobenzoyl)-aminopropyl]-4'-chloroaniline, m.p. 98°–99° C.;

N-methyl-N-(2-hydroxy-3-benzoylaminopropyl)-4'-methylaniline, m.p. 115° C.;

N-methyl-N-(2-hydroxy-3-benzoylaminopropyl)-4'-methoxyaniline, m.p. 120° C.;

N-methyl-N-[2-hydroxy-3-(3'-trifluoromethylbenzoyl)-aminopropyl]-4'-chloroaniline, (oil);

N-benzyl-N-(2-hydroxy-3-benzoylaminopropyl)-4'-chloroaniline, m.p. 128°–132° C.

UTILITY

As already stated in the background chapter of this application the compounds of the invention are principally useful as the starting products for making the 2,3-dihydro-1H-1,4-benzodiazepins disclosed in the U.S. application Ser. No. 355,986 above listed. The conversion of the diaminopropanes to the benzodiazepins can be accomplished by different methods.

A direct conversion to the benzodiazepins can be effected by subjecting the diamonopropane of formula I to the action of a phosphorus oxyhalide, preferably phosphorus oxychloride which may be used by itself or in admixture with phosphorus pentoxide or phosphorus pentachloride. There is then obtained the benzodiazepin of formula II which may indicate various substituents as above indicated with regard to $R_1$, A and B and wherein $R_2$ is halogen, particularly chlorine or bromine. The temperature of the reaction preferably is between 110° and 120° C.

This compound can then be further converted into the desired benzodiazepin wherein $R_2$ has a meaning other than halogen such as hydroxy, alkoxy, etc.

Below the cyclization temperature it is also possible to isolate the intermediate products in the form of the diaminopropanes of the formula I above, in which, however, the hydroxyl group is substituted by halogen.

Further details of this process are described in the mentioned application Ser. No. 355,986.

The diaminopropanes can also form the starting products for making diazocins which latter may further be converted to the benzodiazepins. Thus, this is an indirect way for making diazepins.

In this process the diaminopropane, if R in formula I above is OH, is heated preferably at a lower temperature, that is, at a temperature between 50° and 100° C. in the presence of a phosphorus oxyhalide, preferably phosphorus oxychloride or phosphorus oxybromide.

There is then obtained a benzodiazocine of the formula

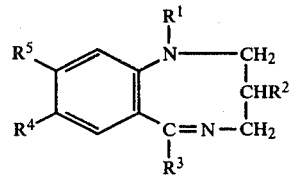

wherein $R_3$ is a phenyl or a phenyl substituted with halogen, methyl, methoxy, etc., and wherein $R_1$ has the meaning above indicated, $R_2$ is halogen or is acyloxy, $R_4$ is a hydrogen, chloro, fluoro, bromo, trifluoromethyl, methyl, methoxy, or methylthio radical, $R_5$ is a hydrogen or methoxy radical. Further details of this process are given in Application Ser. No. 588,969.

The 8-member benzodiazocins which are themselves valuable tranquilizers can further be converted to the benzodiazepins by a ring contraction reaction described in greater detail in Application Ser. No. 598,880 of the same inventors, filing data July 24, 1975, which is a continuation-in-part of application Ser. No. 355,989, filing date May 1, 1973.

We claim:

1. A 1,3-diaminopropane having the formula I

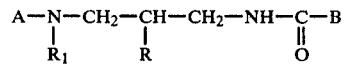

wherein $R_1$ is a member selected from the group consisting of hydrogen, lower alkyl, methoxyethyl, benzyl and cycloalkyl, R is hydroxy, A and B are each a member selected from the group of phenyl, phenyl substituted with 1 to 3 members of the group consisting of halogen, alkyl, alkoxy, nitro, trifluoromethyl, methylthioalkyl and alkoxy, or an acid addition salt of said diaminopropane.

2. A 1,3-diaminopropane according to claim 1, wherein $R_1$ is a member selected from the group consisting of hydrogen, methyl, cyclopropylmethyl and benzyl, A is a member selected from the group consisting of phenyl, 4-fluorophenyl, 4-chlorophenyl, 4-methylphenyl and 4-methoxyphenyl and B is a member selected from the group consisting of phenyl, 2-fluorophenyl, 2-chlorophenyl, 2-trifluoromethylphenyl, 3-trifluoromethylphenyl, 2,4-dichlorophenyl, 3,4-dichlorophenyl, 3,4-dimethoxyphenyl and 3,4,5-trimethoxyphenyl.

3. The compound of claim 1, which is N-methyl-N-(2-hydroxy-3-aminopropyl)-4'-chloroaniline.

4. The compound of claim 1 which is N-methyl-N-(2'-hydroxy-3'-benzoylaminopropyl)-4-chloroaniline.

5. The compound of claim 1 which is N-methyl-N-[2'-hydroxy-3'-(2''-fluorobenzoyl)-aminopropyl]-4-chloroaniline.

6. The compound of claim 1 which is N-methyl-N-[2'-hydroxy-3'-(3'',4'',5''-trimethoxybenzoyl)-aminopropyl]-aniline.

7. The compound of claim 1 which is N-methyl-N-(2'-hydroxy-3'-benzoylaminopropyl)-4-fluoroaniline.

8. The compound of claim 1 which is N-methyl-N-(2'-hydroxy-3'-benzoylaminopropyl)-aniline.

9. The compound of claim 1 which is N-(2'-hydroxy-3'-benzoylaminopropyl)-4-chloroaniline.

10. The compound of claim 1 which is N-cyclopropylmethyl-N-(2'-hydroxy-3'-benzoylaminopropyl)-4-chloroaniline.

11. The compound of claim 1 which is N-methyl-N-[2'-hydroxy-3'-(2'''-chlorobenzoyl)-aminopropyl]-4-chloroaniline.

12. The compound of claim 1 which is N-methyl-N-[2'-hydroxy-3'-(2''-trifluoromethylbenzoyl)-aminopropyl]-4-chloroaniline.

13. The compound of claim 1 which is N-methyl-N-[2'-hydroxy-3'-(3'',4''-dichlorobenzoyl)-aminopropyl]-4-chloroaniline.

14. The compound of claim 1 which is N-methyl-N-[2'-hydroxy-3'-(2'',4''-dichlorobenzoyl)-aminopropyl]-4-chloroaniline.

15. The compound of claim 1 which is N-methyl-N-(2'-hydroxy-3'-benzoylaminopropyl)-4-methylaniline.

16. The compound of claim 1 which is N-methyl-N-(2'-hydroxy-3'-benzoylaminopropyl)-4-methoxyaniline.

17. The compound of claim 1 which is N-methyl-N-[2'-hydroxy-3'-(3'',4''-dimethoxybenzoyl)-aminopropyl]-4-chloroaniline.

18. The compound of claim 1 which is N-benzyl-N-(2'-hydroxy-3'-benzoylaminopropyl)-4-chloroaniline.

19. The compound of claim 1 which is N-methyl-N-[2'-hydroxy-3'-(3''-trifluoromethylbenzoyl)-aminopropyl]-4-chloroaniline.

* * * * *